(12) United States Patent
O'Lenick et al.

(10) Patent No.: US 7,335,627 B1
(45) Date of Patent: Feb. 26, 2008

(54) POLYMERIC ALKYLPOLYGLYCOSIDE CARBOXYLATES

(75) Inventors: Kevin Anthony O'Lenick, Dacula, GA (US); Anthony J. O'Lenick, Jr., Dacula, GA (US)

(73) Assignee: Surfa Tech Corporation, Dacula, GA (US)

(*) Notice: Subject to any disclaimer, the term of this patent is extended or adjusted under 35 U.S.C. 154(b) by 142 days.

(21) Appl. No.: 11/439,934

(22) Filed: May 25, 2006

(51) Int. Cl.
*C11D 1/04* (2006.01)
*C11D 3/22* (2006.01)
*C11D 3/37* (2006.01)
*C07H 15/00* (2006.01)
*A61K 31/715* (2006.01)

(52) U.S. Cl. .............. 510/151; 510/130; 510/470; 510/474; 424/401; 424/418; 424/488; 424/70.13; 514/23; 514/25; 536/1.11; 536/4.1; 536/18.5; 536/123.1; 536/124

(58) Field of Classification Search ............... 510/130, 510/151, 470, 474; 424/401, 418, 488, 70.13; 514/23, 25; 536/4.1, 18.5, 123.1, 124, 1.11
See application file for complete search history.

(56) References Cited

U.S. PATENT DOCUMENTS

| | | | |
|---|---|---|---|
| 5,908,928 A | * | 6/1999 | Milstein et al. .............. 536/120 |
| 6,248,792 B1 | | 6/2001 | Lazarowitz |
| 6,627,612 B1 | | 9/2003 | O'Lenick |

* cited by examiner

*Primary Examiner*—Brian Mruk

(57) ABSTRACT

The products of the invention are polymers of carboxylated alkylpolyglycosides. The products are very mild surfactants that are useful in personal care applications.

9 Claims, No Drawings

POLYMERIC ALKYLPOLYGLYCOSIDE CARBOXYLATES

FIELD OF THE INVENTION

The present invention generally relates to polymeric carboxylated alkyl polyglycosides useful as mild detergents that are biodegradable.

BACKGROUND OF THE INVENTION

Alkyl polyglycosides are used as nonionic surfactants generally used in industrial formulations, for example, like dishwashing detergents. Because they are made from biodegradable, renewable resources like sugar and coconut fatty alcohol there has been much interest in use of these materials in personal care applications. In order to improve the functionality of these materials in personal care applications many derivatives have been made.

Of particular interest is U.S. Pat. No. 6,248,792 to Lazarowitz issued Jun. 19, 2001 discloses "Use of carboxylate alkyl polyglycoside surfactant to increase the foam of other anionic surfactants" The patent, incorporated herein by reference discloses the use of a carboxylated alkyl polyglycoside in combination with an anionic surfactant to increase foam. The carboxylated alkyl polyglycoside, according to the invention, can be the reaction product of an alkyl polyglycoside with an alpha- or 2-halocarboxylic acid; the reaction product of an alkyl polyglycoside with an alpha, beta-unsaturated carboxylic acid; or the reaction product of an alkyl polyglycoside with a cyclic carboxylic acid anhydride. This interesting molecule addresses one aspect of improving the properties of polyglycosides. The problem with such an approach is that the molecule is a monomer. That is a low molecular weight product. We have surprisingly found that this raw material is an outstanding raw material in the preparation of polymers that do not penetrate and de-fat skin, provide outstanding detergency and are outstanding surfactants for the personal care market.

A variety of carboxylated alkyl polyglycoside surfactants can be used as raw materials according to the present invention. The carboxylated alkyl polyglycosides have been made by Cognis using such methods as the reaction of an alkyl polyglycoside with an alpha- or 2-halocarboxylic acid such as 2-chloroacetic acid as described in application Ser. No. 09/013,384 filed Jan. 26, 1998, the entire contents of which are herein incorporated by reference; or by the reaction of an alkyl polyglycoside with an alpha, beta-unsaturated carboxylic acid such as acrylic acid or methacrylic acid; or by the reaction of an alkyl polyglycoside with a cyclic carboxylic acid anhydride such as succinic anhydride or maleic anhydride. The carboxylated alkyl polyglycoside, according to the invention, can therefore be the reaction product of an alkyl polyglycoside with an alpha- or 2-halocarboxylic acid; the reaction product of an alkyl polyglycoside with an alpha, beta-unsaturated carboxylic acid; or the reaction product of an alkyl polyglycoside with a cyclic carboxylic acid anhydride.

U.S. Pat. No. 5,908,928 Milstein, et al issued Jun. 1, 1999 entitled Alkyl polyglycoside ether carboxylates, incorporated herein by reference discloses raw materials used in the preparation of the polymers of the present invention.

SUMMARY OF THE INVENTION

The present invention relates to polymeric carboxylated alkyl polyglycoside made by the reaction of a carboxylated alkyl polyglycoside, with 1,3 dichloro 2-propanol in aqueous solution. The raw material carboxylated alkyl polyglycoside can be made by the reaction of an alpha- or 2-halocarboxylic acid; the reaction product of an alkyl polyglycoside with an alpha, beta-unsaturated carboxylic acid; or the reaction product of an alkyl polyglycoside with a cyclic carboxylic acid anhydride to give heretofore unknown polymeric surfactants.

DESCRIPTION OF THE INVENTION

Other than in the operating examples, or where otherwise indicated, all numbers expressing quantities of ingredients or reaction conditions are to be understood as being modified in all instances by the term "about". All temperatures referenced unless otherwise noted are degrees centigrade, all percentages are percentages by weight, and all references cited, to the degree allowable are incorporated herein by reference.

It has surprisingly been discovered that the reaction of a carboxylated alkyl polyglycoside surfactant with 1,3, dichloro 2 propanol results in a polymeric surfactant that is high molecular weight, has a very lubricious feel on the skin, provides softness to the skin, sometimes called conditioning and is very mild to the skin and eye. These properties make the compounds of the present invention of major importance in personal care formulations.

Compounds of the present invention conform to the following structure;

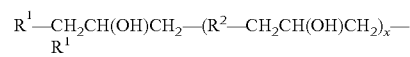

wherein;
$R^1$

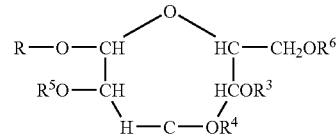

wherein
one of $R^3$, $R^4$, $R^5$, and $R^6$ is covalently bonded through the
—$CH_2$—$CH(OH)CH_2$—;
one other of $R^3$, $R^4$, $R^5$, and $R^6$ is selected from the group consisting of —$CH_2C(O)O^-$ $M^+\!\setminus$ and —$C(O)(CH_2)_2C(O)$ $O^-$ $M^+$
all other $R^3$, $R^4$, $R^5$, and $R^6$ not bonded as specified above are bonded to H;
M is selected from the group consisting of H, Na, and K;
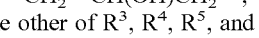
$R^2$ is

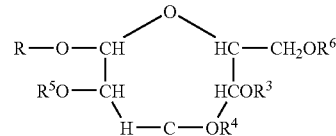

wherein
two or more of $R^3$, $R^4$, $R^5$, and $R^6$ is covalently bonded through a —$CH_2$—$CH(OH)CH_2$—;

one other of $R^3$, $R^4$, $R^5$, and $R^6$ is selected from the group consisting of —$CH_2C(O)O^- M^+$\ and —$C(O)(CH_2)_2C(O)O^- M^+$ all other $R^3$, $R^4$, $R^5$, and $R^6$ not bonded as specified above are bonded to H;

M is selected from the group consisting of H, Na, and K;

R is alkyl having 6 to 30 carbon atoms;

x is an integer ranging from 0 to 20.

Another aspect of the present invention is a process for conditioning skin which comprises contacting the skin with an effective conditioning concentration of a carboxylated polymeric polyglycoside surfactant made by the reaction of (a) a polyglycoside conforming to the following structure:

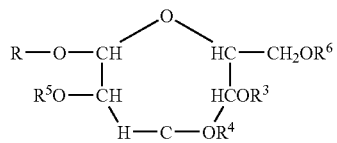

wherein one of $R^3$, $R^4$, $R^5$, and $R^6$ is selected from the group consisting of —$CH_2C(O)O^- M^+$\ or —$C(O)(CH_2)_2C(O)O^- M^+$ all other $R^3$, $R^4$, $R^5$, and $R^6$ not bonded as specified above are bonded to H;

R is alkyl having 6 to 30 carbon atoms.

and (b) 1,3 dichloro-2-propane in water.

The effective conditioning concentration ranges from 0.1% to 25% by weight.

Reaction Sequence

The hydroxyl groups present on the starting material glycoside are reacted with 1,3 dichloro, 2-propanol in aqueous solution, under alkaline conditions to provide the polymer of the present invention. The hydroxyl groups lack a high degree of group specificity and consequently picking one to react over the others is merely a matter of showing one of a variety of materials produced using the process of the current invention.

This lack of high degree of group specificity makes the composition of the present invention best claimed in product by process language.

One of the many reactions is shown below

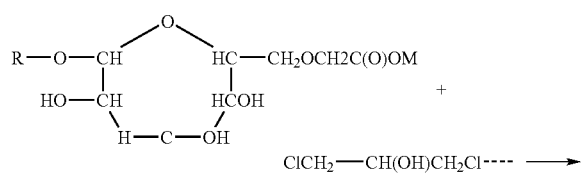

First addition:

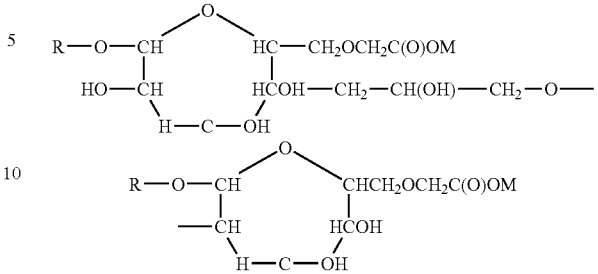

The above compound is when x=0.

When additional 1,3 dichloro 2 propanol is added the x value increases forming a polymer, resulting in the following $R^2$ group;

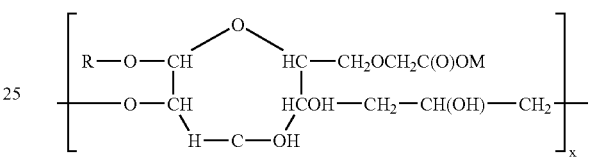

As the value of "x" increases, the viscosity of the product increases and the slip on the skin increases, providing a mild polymeric surfactant that is outstanding in personal care applications.

The present invention is directed to a carboxylated polymeric polyglycoside surfactant made by the reaction of (a) a polyglycoside conforming to the following structure:

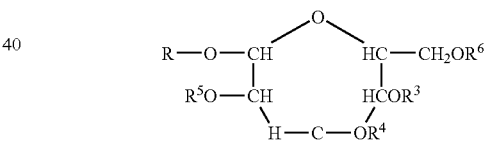

wherein one of $R^3$, $R^4$, $R^5$, and $R^6$ is selected from the group consisting of —$CH_2C(O)O^- M^+$\ or —$C(O)(CH_2)_2C(O)O^- M^+$ all other $R^3$, $R^4$, $R^5$, and $R^6$ not bonded as specified above are bonded to H;

R is alkyl having 6 to 30 carbon atoms.

and (b) 1,3 dichloro-2-propane in water.

PREFERRED EMBODIMENTS

In a preferred embodiment one of $R^3$, $R^4$, $R^5$, and $R^6$ is —$CH_2C(O)O^- M^+$ In a preferred embodiment one of $R^3$, $R^4$, $R^5$, and $R^6$ is —$C(O)(CH_2)_2C(O)O^- M^+$ In a preferred embodiment M is Na.

In a preferred embodiment M is K.

EXAMPLES

Raw Material

Example 1 1,3 dichloro2-propanol

This material is an item of commerce and conforms to the following structure:

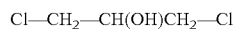
Cl—CH$_2$—CH(OH)CH$_2$—Cl

Example 2-9

The raw material compounds used in the present invention are described U.S. Pat. No. 5,908,928. The raw material for the preparation of the carboxylates which is in turn a raw material for the polymeric compounds of the present invention are commercially available from Cognis. The commercial names are given merely for reference. The compositions were verified by analytical technology including wet methods (hydroxyl value, and C-13 nmr).

Example 2 Preparation of the APG Carboxylate

A mixture of 650 grams (one mole) of a C 12-16 alkyl polyglycoside (commercially available from Cognis as GLUCOPON. 625) having an average degree of polymerization of 1.4 and 700 ml of toluene were heated in order to azeotropically distill any water present in the alkyl polyglycoside, using a Dean Stark trap. The temperature of the mixture rose from 85° C. to 110° C. The distillation required about 4 hours. The dry alkyl polyglycoside was clearly soluble in the toluene at room temperature. To this mixture, 485 grams (one mole) of ethanolic sodium hydroxide was added, with agitation. When the addition was complete, the reaction mixture was heated to about 60° C. for about 1 hour, at which time 116.5 grams (one mole) of sodium monochloroacetate was added, with stirring, and was refluxed for about 5 hours. Water was then added in 200 ml increments while distilling, in 200 ml increments, the ternary azeotrope (toluene/ethanol/water) until the pot temperature reached about 100° C. and only water remained in the product. This required about 8 hours. The distillate came off as two layers: the top layer being rich in toluene, and the bottom layer being rich in water. The top layer was used to azeotropically dry the next batch of alkyl polyglycoside starting material, the distillate initially consisting of the ternary azeotrope, toluene/ethanol/water, and finishing as the binary azeotrope, toluene/water.

Examples 3-9

Example 2 is repeated, only this time replacing the above mentioned C 12-16 alkyl polyglycoside (commercially available from Cognis as GLUCOPON. 625 with the same amount of the following APG.

Example 3

APG 225 Surfactant—an alkyl polyglycoside in which the alkyl group contains 8 to 10 carbon atoms and has an average degree of polymerization of 1.7.

Example 4

GLUCOPON 425 Surfactant—an alkyl polyglycoside in which the alkyl group contains 8 to 16 carbon atoms and has an average degree of polymerization of 1.55.

Example 5

APG 325 Surfactant—an alkyl polyglycoside in which the alkyl groups contain 9 to 11 carbon atoms and have an average degree of polymerization of 1.6.

Example 6

GLUCOPON 600 Surfactant—an alkyl polyglycoside in which the alkyl groups contain 12 to 16 carbon atoms and have an average degree of polymerization of 1.4.

Example 7

PLANTAREN 2000 Surfactant—a C8-16 alkyl polyglycoside in which the alkyl group contains 8 to 16 carbon atoms and has an average degree of polymerization of 1.5.

Example 8

PLANTAREN. 1300 Surfactant—a C.sub.12-16 alkyl polyglycoside in which the alkyl groups contain 12 to 16 carbon atoms and have an average degree of polymerization of 1.6.

Example 9

PLANTAREN 1200 Surfactant—a C.sub.12-16 alkylpolysaccharide in which the alkyl groups contain 12 to 16 carbon atoms and have an average degree of polymerization of 1.4.

Example 10 Preparation of the APG Succinate

A mixture of 650 grams (one mole) of a C 12-16 alkyl polyglycoside (commercially available from Cognis as GLUCOPON. 625) having an average degree of polymerization of 1.4 and 700 ml of toluene were heated in order to azeotropically distill any water present in the alkyl polyglycoside, using a Dean Stark trap. The temperature of the mixture rose from 85° C. to 110° C. The distillation required about 4 hours. The dry alkyl polyglycoside was clearly soluble in the toluene at room temperature. To this mixture, 485 grams (one mole) of ethanolic sodium hydroxide was added, with agitation. When the addition was complete, the reaction mixture was heated to about 60° C. for about 1 hour, at which time grams (one mole) of succinic anhydride 101.0 was added, with stirring, and was refluxed for about 5 hours. Water was then added in 200 ml increments while distilling, in 200 ml increments, the ternary azeotrope (toluene/ethanol/water) until the pot temperature reached about 100° C. and only water remained in the product. This required about 8 hours. The distillate came off as two layers: the top layer being rich in toluene, and the bottom layer being rich in water. The top layer was used to azeotropically dry the next batch of alkyl polyglycoside starting material, the distillate initially consisting of the ternary azeotrope, toluene/ethanol/water, and finishing as the binary azeotrope, toluene/water.

Examples 11-17

Example 10 is repeated, only this time replacing the above mentioned C 12-16 alkyl polyglycoside (commercially available from Cognis as GLUCOPON. 625 with the same amount of the following APG.

Example 11

APG 225 Surfactant—an alkyl polyglycoside in which the alkyl group contains 8 to 10 carbon atoms and has an average degree of polymerization of 1.7.

Example 12

GLUCOPON 425 Surfactant—an alkyl polyglycoside in which the alkyl group contains 8 to 16 carbon atoms and has an average degree of polymerization of 1.55.

Example 13

APG 325 Surfactant—an alkyl polyglycoside in which the alkyl groups contain 9 to 11 carbon atoms and have an average degree of polymerization of 1.6.

Example 14

GLUCOPON 600 Surfactant—an alkyl polyglycoside in which the alkyl groups contain 12 to 16 carbon atoms and have an average degree of polymerization of 1.4.

Example 15

PLANTAREN 2000 Surfactant—a C8-16 alkyl polyglycoside in which the alkyl group contains 8 to 16 carbon atoms and has an average degree of polymerization of 1.5.

Example 16

PLANTAREN. 1300 Surfactant—a C.sub.12-16 alkyl polyglycoside in which the alkyl groups contain 12 to 16 carbon atoms and have an average degree of polymerization of 1.6.

Example 17

PLANTAREN 1200 Surfactant—a C.sub.12-16 alkylpolysaccharide in which the alkyl groups contain 12 to 16 carbon atoms and have an average degree of polymerization of 1.4.

Preparation of Polymers

To the specified number of grams of the specified APG derivative (Examples 2-17) is added enough water to make a 35% solution. Next the specified number of grams of 1,3 dichloro-2-propanol (Example 1) is added and the pH is adjusted to 8 with KOH. Next the temperature is raised to 80-90° C. and the temperature and pH is held for 8 hours. The theoretical amount of water is distilled off during this time.

The larger the number of grams of Example 1, the greater the "x" value in the formula.

The product is cooled and used without purification

| Example | APG Raw Material Example | Grams | 1,3,dichloro-2-propane Grams |
|---|---|---|---|
| 18 | 2 | 500.0 | 100.0 |
| 19 | 3 | 500.0 | 50.0 |
| 20 | 4 | 500.0 | 200.0 |
| 21 | 5 | 500.0 | 177.6 |
| 22 | 6 | 500.0 | 50.0 |
| 23 | 7 | 500.0 | 100.0 |
| 24 | 8 | 500.0 | 300.0 |

-continued

| Example | APG Raw Material Example | Grams | 1,3,dichloro-2-propane Grams |
|---|---|---|---|
| 25 | 9 | 500.0 | 50.0 |
| 26 | 10 | 500.0 | 75.0 |
| 27 | 11 | 500.0 | 100.0 |
| 28 | 12 | 500.0 | 250.0 |
| 20 | 13 | 500.0 | 70.0 |
| 30 | 14 | 500.0 | 80.0 |
| 31 | 15 | 500.0 | 145.0 |
| 32 | 16 | 500.0 | 300.0 |
| 33 | 17 | 500.0 | 25.0 |

APPLICATIONS EXAMPLES

The products of the present invention are clear yellow liquids that have good foam attributes. They are very mild to the skin and eye and are good detergents.

While the illustrative embodiments of the invention have been described with particularity, it will be understood that various other modifications will be apparent to, and can be readily made by, those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A carboxylated polymeric polyglycoside surfactant made by the reaction of (a) a polyglycoside conforming to the following structure:

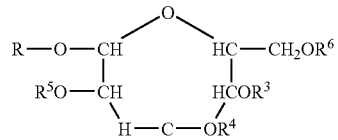

wherein
one of $R^3$, $R^4$, $R^5$, and $R^6$ is selected from the group consisting of —$CH_2C(O)O^-$ $M^+$\ or —$C(O)(CH_2)_2C(O)O^-M^+$ all other $R^3$, $R^4$, $R^5$, and $R^6$ not bonded as specified above are bonded to H;

R is alkyl having 6 to 30 carbon atoms M is selected from the group consisting of H, Na, and K;

and (b) 1,3 dichloro-2-propanol
in water.

2. A carboxylated polymeric polyglycoside of claim 1 wherein at least one of $R^3$, $R^4$, $R^5$, and $R^6$ is —$CH_2C(O)O^-$ $M^+$.

3. A carboxylated polymeric polyglycoside of claim 1 wherein at least one of $R^3$, $R^4$, $R^5$, and $R^6$ is —$C(O)(CH_2)_2C(O)O^-$ $M^+$.

4. A process for conditioning skin which comprises contacting the skin with an effective conditioning concentration of a carboxylated polymeric polyglycoside surfactant made by the reaction of (a) a polyglycoside conforming to the following structure:

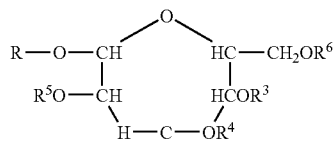

wherein
one of $R^3$, $R^4$, $R^5$, and $R^6$ is selected from the group consisting of —$CH_2C(O)O^- M^+$\ or —$C(O)(CH_2)_2C(O)O^- M^+$
all other $R^3$, $R^4$, $R^5$, and $R^6$ not bonded as specified above are bonded to H;
R is alkyl having 6 to 30 carbon atoms M is selected from the group consisting of H, Na, and K;

and
(b) 1,3 dichloro-2-propanol
in water.

5. A process of claim 4 wherein said effective conditioning concentration ranges from 0.1% to 25% by weight.

6. A process of claim 4 wherein at least one of $R^3$, $R^4$, $R^5$, and $R^6$ is —$CH_2C(O)O^- M^+$.

7. A process of claim 4 wherein at least one of $R^3$, $R^4$, $R^5$, and $R^6$ is —$C(O)(CH_2)_2C(O)O^- M^+$.

8. A process of claim 5 wherein at least one of $R^3$, $R^4$, $R^5$, and $R^6$ is —$CH_2C(O)O^- M^+$.

9. A process of claim 5 wherein at least one of $R^3$, $R^4$, $R^5$, and $R^6$ is —$C(O)(CH_2)_2C(O)O^- M^+$.

* * * * *